United States Patent
Petitprez et al.

(10) Patent No.: US 12,295,785 B2
(45) Date of Patent: May 13, 2025

(54) CLEANABLE AND STERILIZABLE ELECTRICAL CONNECTOR FOR MEDICAL DEVICES

(71) Applicant: GE Precision Healthcare LLC, Wauwatosa, WI (US)

(72) Inventors: Matthieu Petitprez, Saint Vallier de Thiey (FR); Edouard Dacruz, Nice (FR); Jean-Marc Baraban, La Roquette sur Siagne (FR); Giandonato Stallone, Nice (FR)

(73) Assignee: GE Precision Healthcare LLC, Waukesha, WI (US)

( * ) Notice: Subject to any disclaimer, the term of this patent is extended or adjusted under 35 U.S.C. 154(b) by 223 days.

(21) Appl. No.: 17/711,713

(22) Filed: Apr. 1, 2022

(65) Prior Publication Data

US 2023/0309959 A1    Oct. 5, 2023

(51) Int. Cl.
*A61B 8/00*    (2006.01)
*H02G 3/00*    (2006.01)

(52) U.S. Cl.
CPC ............. *A61B 8/4422* (2013.01); *H02G 3/00* (2013.01)

(58) Field of Classification Search
CPC ............ A61B 8/4422; A61B 8/00; H02G 3/00
USPC ....................................................... 174/68.1
See application file for complete search history.

(56) References Cited

U.S. PATENT DOCUMENTS

| | | |
|---|---|---|
| 5,678,551 A | 10/1997 | Stevens |
| 7,297,115 B2 | 11/2007 | Bates et al. |
| 11,095,068 B2 | 8/2021 | Al-Ali et al. |
| 2013/0146615 A1* | 6/2013 | Gaudet .................. G05D 13/02 604/131 |
| 2016/0365673 A1* | 12/2016 | Liang ................. H01R 13/6469 |
| 2018/0202962 A1 | 7/2018 | Simmons et al. |

* cited by examiner

*Primary Examiner* — Tremesha W Burns
(74) *Attorney, Agent, or Firm* — McAndrews, Held & Malloy, Ltd.; Daniel Bissing; David Bates

(57) ABSTRACT

Systems and methods are provided for cleanable and sterilizable electrical connector for medical devices. A sterilizable connector may include a first shell and a second shell configured to engage one another, a nose housing that includes a mating area of the connector for engaging a corresponding mating area in a component of a medical device, and an overmolding that overmolds a combination of the first shell, the second shell, and the nose housing. Each of the first shell, the second shell, and the nose housing includes a first material that is compatible with cleaning and sterilization (C&S) treatment. The overmolding includes a second material that provides sealing of the combination of the first shell, the second shell, and the nose housing during the cleaning and sterilization (C&S) treatment. The connector is configured to enable applying at least sterilization without requiring closing or covering of the mating area of the connector.

16 Claims, 7 Drawing Sheets

CLEANABLE AND STERILIZABLE ELECTRICAL CONNECTOR FOR MEDICAL DEVICES

FIELD

Aspects of the present disclosure relate to medical imaging solutions. More specifically, certain embodiments relate to methods and systems for cleanable and sterilizable electrical connector for medical devices.

BACKGROUND

Various medical imaging techniques may be used, such as in imaging organs and soft tissues in a human body. Examples of medical imaging techniques include ultrasound imaging, computed tomography (CT) scans, magnetic resonance imaging (MRI), etc. The manner by which images are generated during medical imaging depends on the particular technique.

For example, ultrasound imaging uses real time, non-invasive high frequency sound waves to produce ultrasound images, typically of organs, tissues, objects (e.g., fetus) inside the human body. Images produced or generated during medical imaging may be two-dimensional (2D), three-dimensional (3D), and/or four-dimensional (4D) images (essentially real-time/continuous 3D images). During medical imaging, imaging datasets (including, e.g., volumetric imaging datasets during 3D/4D imaging) are acquired and used in generating and rendering corresponding images (e.g., via a display) in real-time.

In some instances, operation of certain components of medical imaging systems, such as the medical imaging probes, may pose certain challenges, particularly in conjunction with conditions that may cause damage to these components, and conventional and traditional approaches may not sufficiently address or overcome these challenges.

Further limitations and disadvantages of conventional and traditional approaches will become apparent to one of skill in the art, through comparison of such systems with some aspects of the present disclosure, as set forth in the remainder of the present application with reference to the drawings.

BRIEF SUMMARY

System and methods are provided for cleanable and sterilizable electrical connector for medical devices, substantially as shown in and/or described in connection with at least one of the figures, as set forth more completely in the claims.

These and other advantages, aspects and novel features of the present disclosure, as well as details of one or more illustrated example embodiments thereof, will be more fully understood from the following description and drawings.

DETAILED DESCRIPTION

Figure 1:
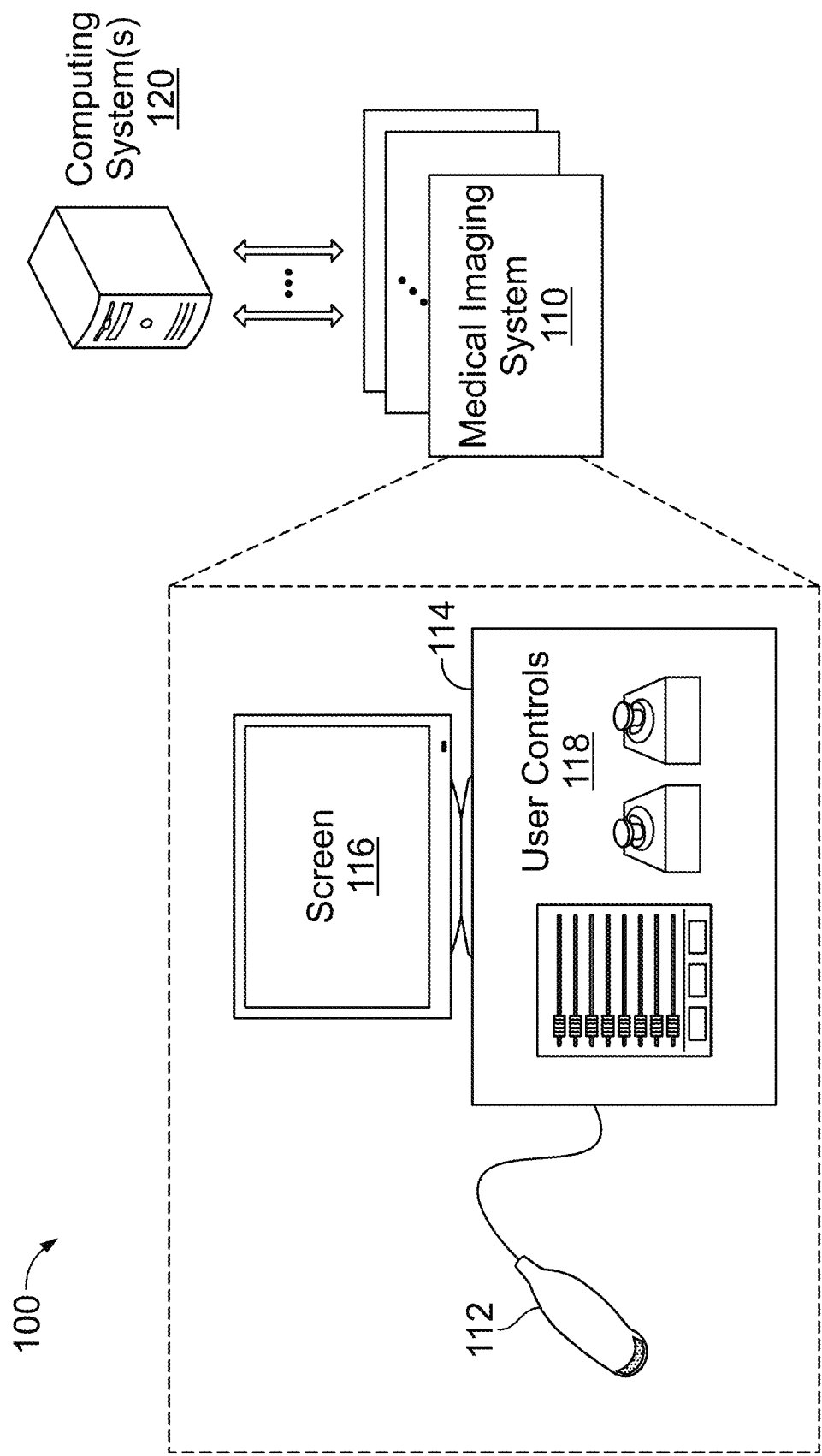
FIG. 1 is a block diagram illustrating an example medical imaging arrangement.

Certain implementations in accordance with the present disclosure may be directed to cleanable and sterilizable electrical connector for medical devices. In particular, the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" as used in the context of ultrasound imaging is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

In addition, as used herein, the phrase "pixel" also includes embodiments where the data is represented by a "voxel." Thus, both the terms "pixel" and "voxel" may be used interchangeably throughout this document.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC, or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". In addition, forming of images may be performed using channel combinations that may originate from more than one transmit event (e.g., synthetic aperture techniques).

In various embodiments, processing to form images is performed in software, firmware, hardware, or a combination thereof. The processing may include use of beamforming.

FIG. 1 is a block diagram illustrating an example medical imaging arrangement. Shown in FIG. 1 is an example medical imaging arrangement 100 that comprises one or more medical imaging systems 110 and one or more computing systems 120. The medical imaging arrangement 100 (including various elements thereof) may be configured to support medical imaging and solutions associated therewith.

The medical imaging system 110 comprise suitable hardware, software, or a combination thereof, for supporting medical imaging—that is enabling obtaining data used in generating and/or rendering images during medical imaging exams. Examples of medical imaging include ultrasound imaging, computed tomography (CT) scans, magnetic resonance imaging (MRI), etc. This may entail capturing of particular type of data, in particular manner, which may in turn be used in generating data for the images. For example, the medical imaging system 110 may be an ultrasound imaging system, configured for generating and/or rendering ultrasound images.

As shown in FIG. 1, the medical imaging system 110 may comprise a scanner device 112, which may be portable and movable, and a display/control unit 114. The scanner device 112 may be configured for generating and/or capturing particular type of imaging signals (and/or data corresponding thereto), such as by being moved over a patient's body (or part thereof), and may comprise suitable circuitry for performing and/or supporting such functions. The scanner device 112 may be an ultrasound probe, MRI scanner, CT scanner, or any suitable imaging device. For example, where the medical imaging system 110 is an ultrasound system, the scanner device 112 may emit ultrasound signals and capture echo ultrasound images.

The display/control unit 114 may be configured for displaying images (e.g., via a screen 116). In some instances, the display/control unit 114 may further be configured for generating the displayed images, at least partly. Further, the display/control unit 114 may also support user input/output. For example, the display/control unit 114 may provide (e.g., via the screen 116), in addition to the images, user feedback (e.g., information relating to the system, functions thereof, settings thereof, etc.). The display/control unit 114 may also support user input (e.g., via user controls 118), such as to allow controlling of the medical imaging. The user input may be directed to controlling display of images, selecting settings, specifying user preferences, requesting feedback, etc.

In some implementations, the medical imaging arrangement 100 may also incorporate additional and dedicated computing resources, such as the one or more computing systems 120. In this regard, each computing system 120 may comprise suitable circuitry, interfaces, logic, and/or code for processing, storing, and/or communication data. The computing system 120 may be dedicated equipment configured particularly for use in conjunction with medical imaging, or it may be a general purpose computing system (e.g., personal computer, server, etc.) set up and/or configured to perform the operations described hereinafter with respect to the computing system 120. The computing system 120 may be configured to support operations of the medical imaging systems 110, as described below. In this regard, various functions and/or operations may be offloaded from the imaging systems. This may be done to streamline and/or centralize certain aspects of the processing, to reduce cost—e.g., by obviating the need to increase processing resources in the imaging systems.

The computing systems 120 may be set up and/or arranged for use in different ways. For example, in some implementations a single computing system 120 may be used; in other implementations multiple computing systems 120, either configured to work together (e.g., based on distributed-processing configuration), or separately, with each computing system 120 being configured to handle particular aspects and/or functions, and/or to process data only for particular medical imaging systems 110. Further, in some implementations, the computing systems 120 may be local (e.g., co-located with one or more medical imaging systems 110, such within the same facility and/or same local network); in other implementations, the computing systems 120 may be remote and thus can only be accessed via remote connections (e.g., via the Internet or other available remote access techniques). In a particular implementation, the computing systems 120 may be configured in cloud-based manner, and may be accessed and/or used in substantially similar way that other cloud-based systems are accessed and used.

Once data is generated and/or configured in the computing system 120, the data may be copied and/or loaded into the medical imaging systems 110. This may be done in different ways. For example, the data may be loaded via directed connections or links between the medical imaging systems 110 and the computing system 120. In this regard, communications between the different elements in the medical imaging arrangement 100 may be done using available wired and/or wireless connections, and/or in accordance any suitable communication (and/or networking) standards or protocols. Alternatively, or additionally, the data may be loaded into the medical imaging systems 110 indirectly. For example, the data may be stored into suitable machine readable media (e.g., flash card, etc.), which are then used to load the data into the medical imaging systems 110 (on-site, such as by users of the systems (e.g., imaging clinicians) or authorized personnel), or the data may be downloaded into local communication-capable electronic devices (e.g., laptops, etc.), which are then used on-site (e.g., by users of the systems or authorized personnel) to upload the data into the medical imaging systems 110, via direct connections (e.g., USB connector, etc.).

In operation, the medical imaging system 110 may be used in generating and presenting (e.g., rendering or displaying) images during medical exams, and/or in supporting user input/output in conjunction therewith. The images may be 2D, 3D, and/or 4D images. The particular operations or functions performed in the medical imaging system 110 to facilitate the generating and/or presenting of images depends on the type of system—that is, the manner by which the data corresponding to the images is obtained and/or generated. For example, in ultrasound imaging, the data is based on emitted and echo ultrasound signals. In computed tomography (CT) scans based imaging, the data is based on emitted and captured x-rays signals.

In various implementations in accordance with the present disclosure, medical imaging systems and/or architectures (e.g., the medical imaging system 110 and/or the medical imaging arrangement 100 as a whole) may be configured to support implementing and utilizing cleanable and sterilizable electrical connectors (e.g., for medical imaging probes used therein). In this regard, in some instances medical imaging systems and/or architectures may include connectors, which may be used therein in connecting components of the systems and/or architectures. For example, medical imaging probes (e.g., the scanner device 112 in the medical imaging system 110 of FIG. 1) may be corded, having cable terminated in connectors having mating area that may be configured to engaging corresponding mating area in another component of the system (e.g., the display/control unit 114 in the medical imaging system 110 of FIG. 1). The connector may be of various types, and/or may be configured based on one of various supported connectors standards. For example, in various instances RS connectors may be used.

In some instances, components of medical imaging systems incorporating connectors may need to be regularly cleaned and sterilized (e.g., between uses, particularly when being used on different patients). In this regard, cleaning and sterilization may typically entail or include subjecting the component to fluids (e.g., water, special cleaning and/or sterilization chemical solutions, etc.), such as by immersing the parts, or portions thereof, in such fluid. This may pose challenges, however, due to the open areas in the connectors—e.g., the mating portion(s), where the connector(s) may engaging corresponding mating areas (e.g., slots of the like) in other component(s) of the medical imaging systems.

Conventional solutions for handling cleaning and sterilization in connectors may have various limitations and disadvantages. For example, in various conventional connector solutions, the connectors, and specially-designed peer devices used therewith during cleaning and sterilization (C&S) treatment, may incorporate extensive and complex parts mechanisms (e.g., locking mechanisms, pumping mechanism (or devices) to maintain high pressure within the mating area, etc.) to secure the connector against ingress of fluids during the C&S treatment. Further, such conventional solutions may require or entail regular checks of the connector (e.g., after each use, periodically, etc.).

Solutions in accordance with the present disclosure may overcome and remedy the limitations and disadvantages of conventional solutions, particularly by incorporating cost-effective and easy-to-use sealing mechanism to ensure that the connectors are protected (e.g., sealed) during cleaning and sterilization. In this regard, with the increase of need to disinfect and sterilize medical equipment, embodiments based on the present disclosure provide user-friendly, reliable, and robust connector solutions (e.g., for probes assemblies used in medical imaging systems. In this regard, while some of the connector solutions described herein are shown in the context of ultrasound probes, the disclosure may be similarly applied to other medical devices. Probe assemblies incorporating connector solutions implemented in accordance with the present disclosure may not require any maintenance activity or proof tests all along its life time. For example, connector based on the present disclosure be qualified for large number of reprocessing cycles (e.g., a 125 reprocessing cycles) without any specific tasks (other than precaution of use). Further, material used in connectors based on the present disclosure may be selected to optimize performance. In this regard, overall reprocessing cycles (from cleaning to disinfection and sterilization) may be characterized by use of stringent chemicals which may deteriorate materials typically used in conventional solutions. The proposed connectors, however, may use materials (e.g., Santoprene and polymer, such as polypropylene or polycarbonate) selected to resist to chemicals used in such reprocessing cycles. In this regard, where Santoprene is used, the Santoprene grade may be adaptively selected, such as to maximize adhesion performances—e.g., with the internal polymer shells used therewith. For example, in some implementations, medical grade Santoprene is used.

Example embodiments based on the present disclosure may include an assembly of a connector with a lid that provides a fully cleanable and sterilizable connector for medical imaging device. The connector can be used for coaxial or standard cables, and may be shielded or not. With the lid applied to the connector, the assembly is robust during cleaning (e.g., versus soaking (e.g., IPX7 rating compliant) and water jetting (e.g., IPX6 rating compliant) processes). With the lid removed, the connectors (or components thereof) are compatible with sterilization processes typically used in hospitals (e.g., low temperature process, with plasma of hydrogen peroxide gas). Performance of the connector (and assembly of connector/lid) may be ensured by use a specific manufacturing process and selection of dedicated materials.

In various example embodiments, the connector casing may be designed and manufactured in order to limit the number of possible leakage point. All the electrical components and/or circuitry (printed boards, cables, solders, etc.) may be located in a housing made with two clamshells and one nose housing press fitted together. The assembly may provide the mechanical robustness (and the shielding in case of a shielded assembly) but every interface between the clamshells remains possible leakage points. In various implementations, the assembly may be overmolded with a specific thermoplastic (e.g., thermoplastic vulcanizate (TPV)) which provide the high level of sealing. As such, the only remaining inlet may be the mating portion of the connector. To close the mating portion, a specific self-locking lid may be used. The lid may be a low-cost simple cap. With such a simple shape, the one interface of possible ingress may secured (sealed), such as with dedicated gaskets. The low-cost aspect makes the lid to be considered as a consumable. In addition, to ensure and/or enhance shielding performance, the connector may incorporate features for mitigating electromagnetic interference (EMI). In this regard, rather than using standard EMI casings, the connector may incorporate casing that comprises a polymer (e.g., polypropylene or polycarbonate) used in combination with conductive shielding (internally) in order to merge the mechanical and electrical purposes.

Accordingly, embodiments in accordance with the present disclosure may offer various technical and commercial advantages over conventional solutions, including, for example, 1) use of materials selected for their robustness versus cleaning, disinfection and sterilization processes; 2) possibility to soak the connector (e.g., in water) for extended period of time (e.g., 30 min), and at substantial depth (e.g., 1 m depth) (that is compliant with IPX7 rating based soaking); 3) possibility to use fluid at high pressure (e.g., water jet process at 30 psi) for cleaning process; 4) possibility to use low temperature sterilization process (e.g., Sterrad 100NX or equivalent); 5) ability to provide a shielded or non-shielded version with the same design, low-cost lid assembly, which may be considered as a consumable; 6) generally being Maintenance free.

Example embodiments and implementations based thereon, and additional details related thereto, are described in more detail below, with respect to FIGS. 2-6.

Figure 2:
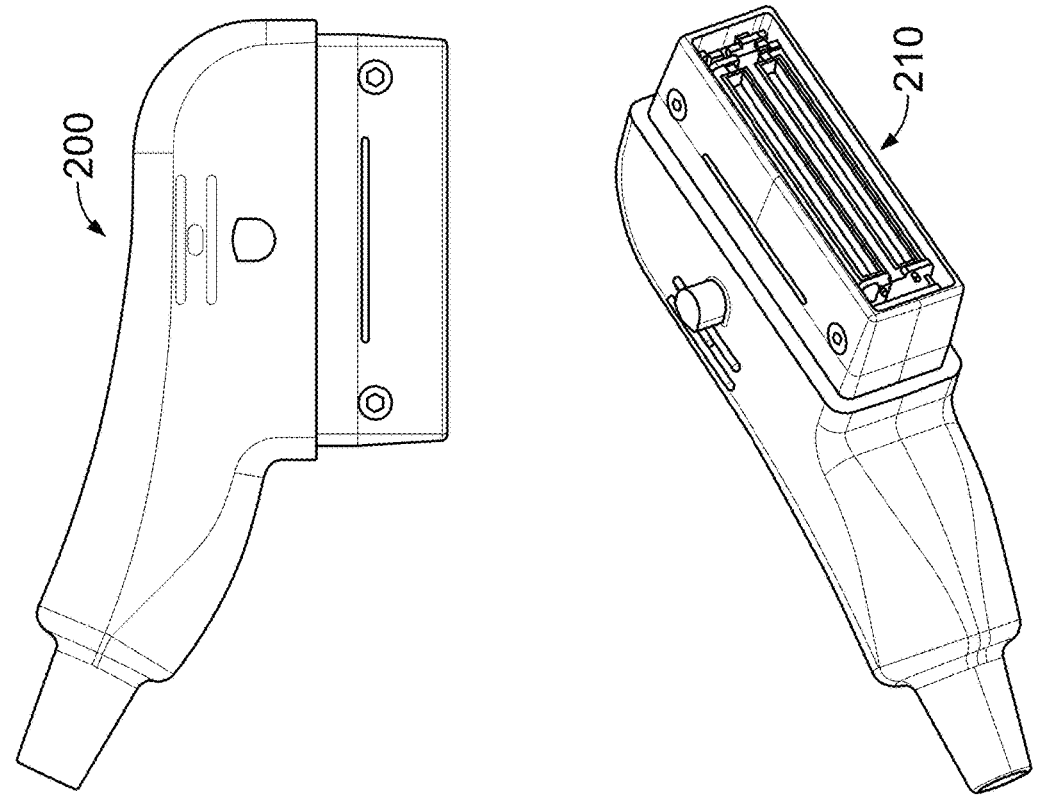
FIG. 2 is a block diagram illustrating an example conventional connector and an example sterilizable connector in accordance with the present disclosure.
Figure 2:
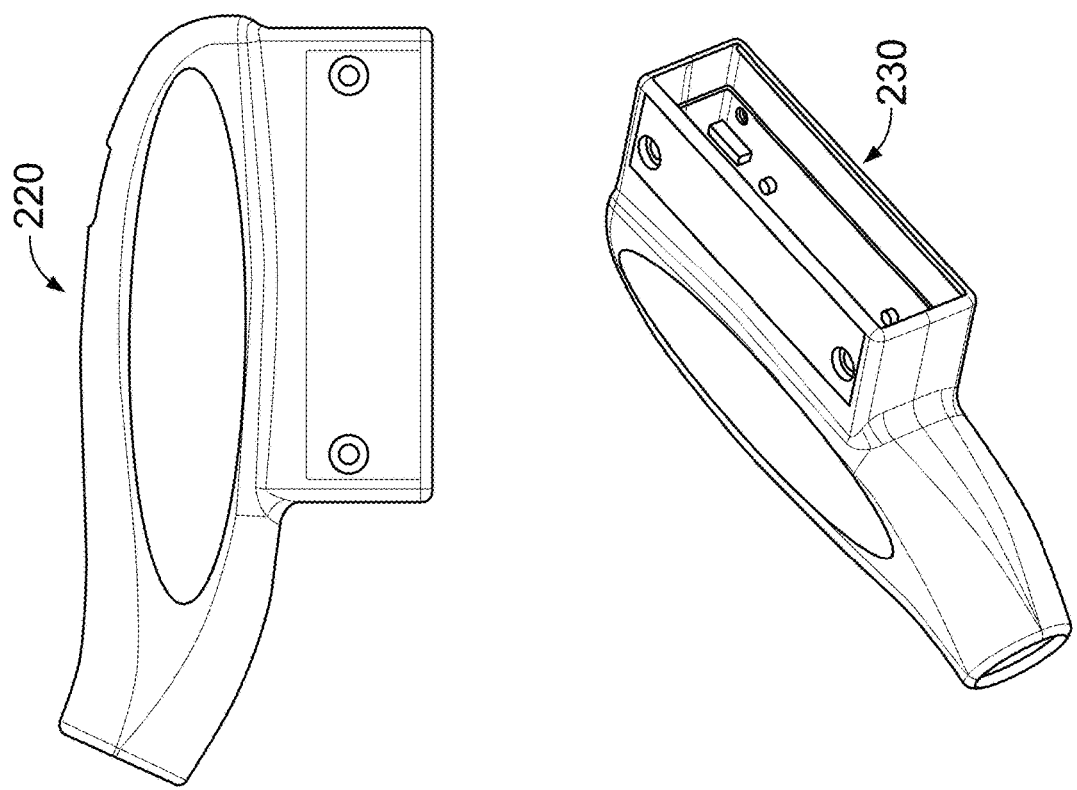

FIG. 2 is a block diagram illustrating an example conventional connector and an example sterilizable connector in accordance with the present disclosure. Shown in FIG. 2 are connectors 200 and 220. In this regard, connector 200 is implemented in accordance with an embodiment of the present disclosure whereas connector 220 is a conventional connector—that is, implemented using conventional approaches, without the features described herein to provide sealed sterilizable connector.

The connector 220, which corresponds to conventional approach, may comprise two clamshells (e.g., casted aluminum shells) combined together, such as using screws or other fastening means, with the assembly as a whole not being sealed, and optionally painted with the paint not being compatible with cleaning and sterilization cycles. The connector 220 includes non-sealed mating portion 230, which is used to engage corresponding mating interface in a component of the medical imaging system. Because of material used in the connector (which may not be compatibility with chemical solutions used in cleaning and sterilization treatment), arrangement of components thereof, and the open (non-sealed) mating portion, the connector 220 lacks compatibility with cleaning and sterilization (C&S) treatment.

The design of connector 200, in contrast, provides compatibility with cleaning and sterilization processing, particularly by incorporating features that optimized performance with respect to C&S treatment in cost-effective manner. In this regard, design of connectors implemented based on the present disclosure may be driven by such consideration as: 1) selection of materials for C&S compatibility; 2) removing leak points for water-tightness; and 3) maintain compatibility with existing systems (e.g., medical imaging consoles).

For example, as shown in FIG. 2, the connector 200 comprise two clamshells and one nose housing (e.g., comprising hard polymer), and the three parts are overmolded together in order to provide a fully sealed assembly. The connector 200 may comprise a mating portion 210, which unlike that of the connector 220, is sealed to enable at least sterilizing the connector 200 as is. A lid (not shown, but described below) may added to close the matting portion 210, such as during cleaning. Material used in the components of the connector 200 may be selected for optimal performance for and compatibility with the C&S treatment (e.g., to ensure water-tightness), and also for other considerations, such as easy of manufacture, medical grade material to ensure bio compatibility thus approval by agencies (FDA)). The overmolded shells and nose housing encapsulate most of the connector (e.g., 80% of it), with the remaining parts (particularly the exposed mating portion 210) being fully sealed, such as using hot temperature process, to allow for sterilization without need to be covered. As such, the connector 200 may be implemented and used without requiring dedicated locking mechanism (or the like). The lid is cheap and simple and thus may be replaced (by itself) while the same connector.

Figure 3:
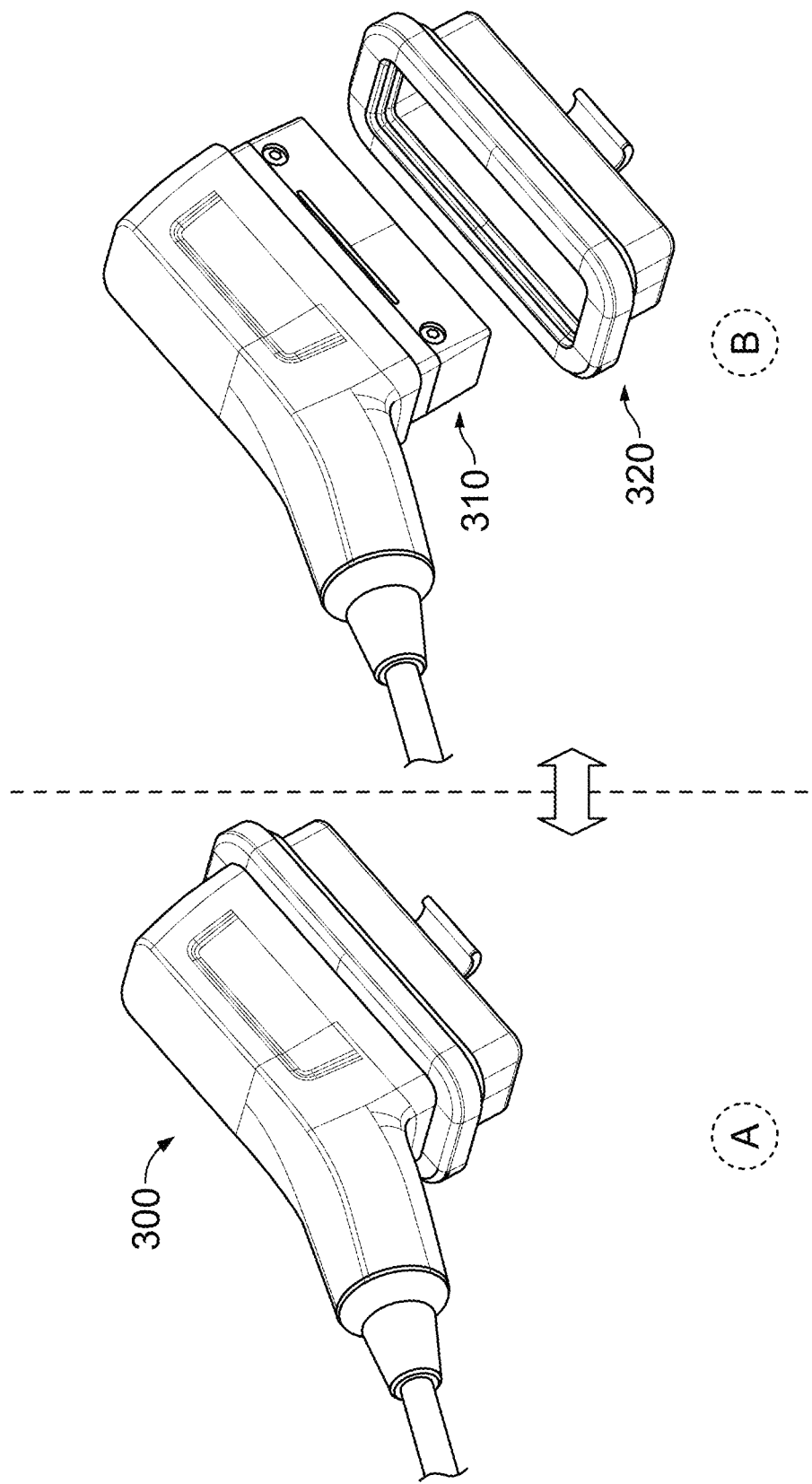
FIG. 3 is a block diagram illustrating an example assembly of sterilizable connector and lid, in accordance with the present disclosure.

FIG. 3 is a block diagram illustrating an example assembly of sterilizable connector and lid, in accordance with the present disclosure. Shown in FIG. 3 is sterilizable connector 300 along with lid 320. The connector 300 may be substantially similar to the connector 200 as described above. The lid 320 may be configured for application to sealable mating portion 310 of the connector 300.

The lid 320 may be selectively applied to the connector 300—that is, the lid 320 may be applied to the connector 300 when needed, and removed when it is not needed. The lid 320 may be required, for example, during cleaning which entail higher probability of fluid ingress, but may not be required during sterilization. For example, in scenario 'A' the lid 320 is applied to the connector 300, making the combined assembly compliant with IPX6 and IPX7 ratings, and as such the assembly may be ready for cleaning/disinfection process into dedicated bath (IPX7 rating based process) and/or waterjet chamber (IPX6 rating based process). In scenario 'B' the lid 320 is removed from the connector 300, which removes the seal of the sealable mating portion 310. Nonetheless, the assembly may be suitable and ready for low temperature sterilization process, such as in dedicated chamber.

Figure 4:
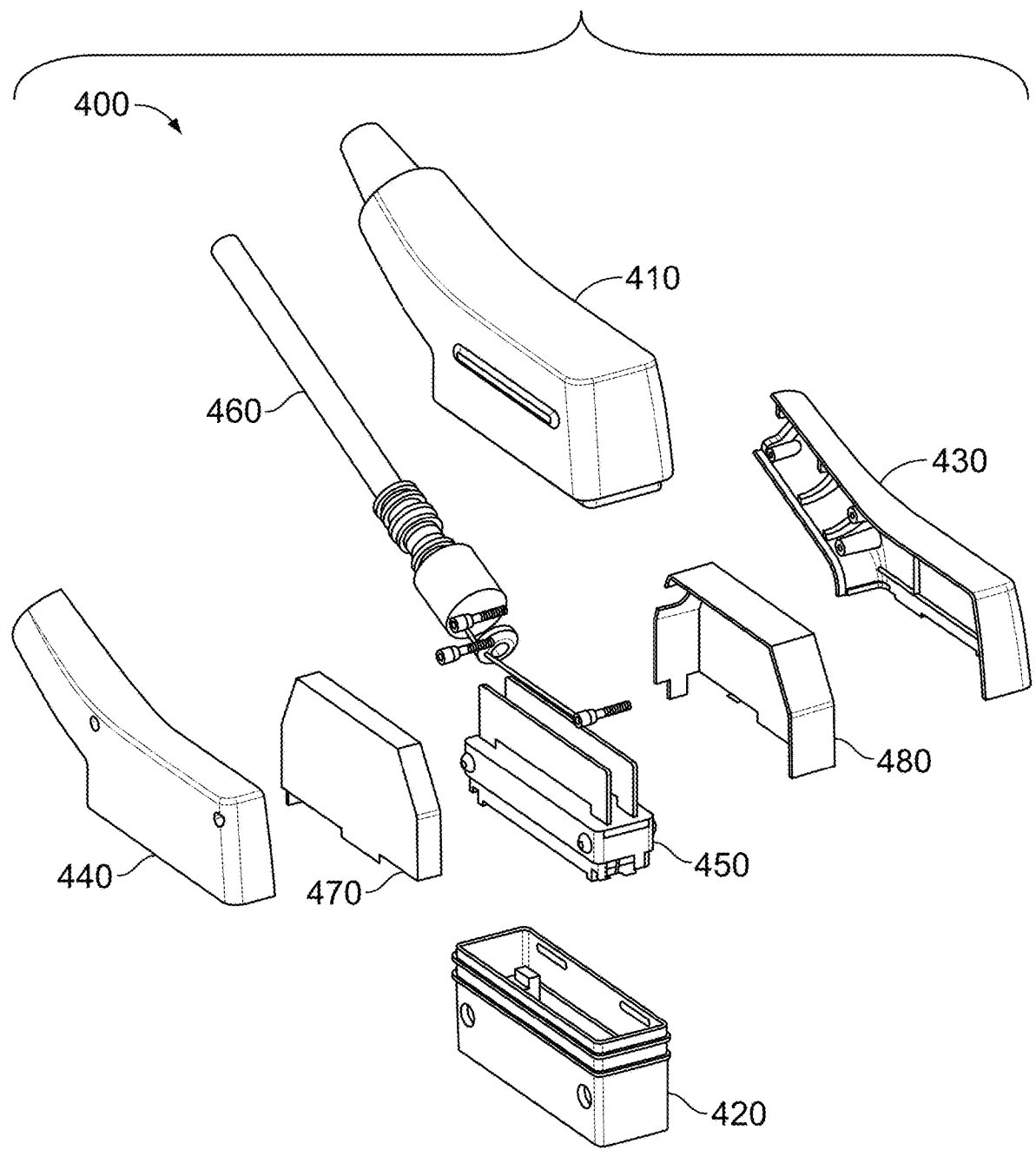
FIG. 4 is a block diagram illustrating components of an example sterilizable connector, in accordance with the present disclosure.

FIG. 4 is a block diagram illustrating components of an example sterilizable connector, in accordance with the present disclosure. Shown in FIG. 4 is sterilizable connector 400. The connector 400 may be substantially similar to, and may represent an example implementation of the connector 200 as described above.

As shown in FIG. 4, the connector As shown in the example embodiment illustrated in FIG. 4, the connector 400 may comprise an overmolding 410, a right clamshell 420, a nose housing 430, a left clamshell 440, a shielded connector/circuitry 450, cable assembly 460, a left shield shell 470, and a right shield shell 480. The material used in at least some of these components to optimize cleaning and sterilization, particularly by providing sealed connector once assembled (e.g., ensure water-tightness), while also optimizing ease of manufacture and compliance with applicable medical regulation.

For example, the overmolding 410 may comprise high performance polymer, such as thermoplastic vulcanizate (e.g., Santoprene 8281-65 Med). The right clamshell 420 and the left clamshell 440 may comprise non-conductive polymer, such as a thermoplastic polymer (e.g., polypropylene or polycarbonate). Similarly, the nose housing 430 may comprise non-conductive polymer, such as a thermoplastic polymer (e.g., polypropylene or polycarbonate). The left shield shell 470 and the right shield shell 480 may be configured for shielding the connector/circuitry 450 from Electromagnetic interference (EMI), and as such may comprise suitable material for that function, such as stamped metal foil.

As noted, the selectin of the material of the components, and the arrangement of the components within the connectors optimize performance of the connector, particularly with respect to the cleaning and sterilization processes. In this regard, the combination of the overmolding 410, the right clamshell 420, and the left clamshell 440 may encapsulate most of the connector (e.g., 80% of it). The overmolding 410 may provide a smooth touch and the full sealing of the interfaces between clamshells 420 and 440 and the nose housing 430. The exposed mating portion of the connector (e.g., interface at the bottom of the shielded connector/circuitry 450) may be fully sealed, such as using hot temperature process, to allow for sterilization without need to be covered. Accordingly, no regular checks of the sealing are required. The hard internal clamshells provide mechanical robustness with a lower weight. The overmolding makes the design applicable to all cable diameter. Further, the use of internal metal shell make the connector shielded.

Figure 5:
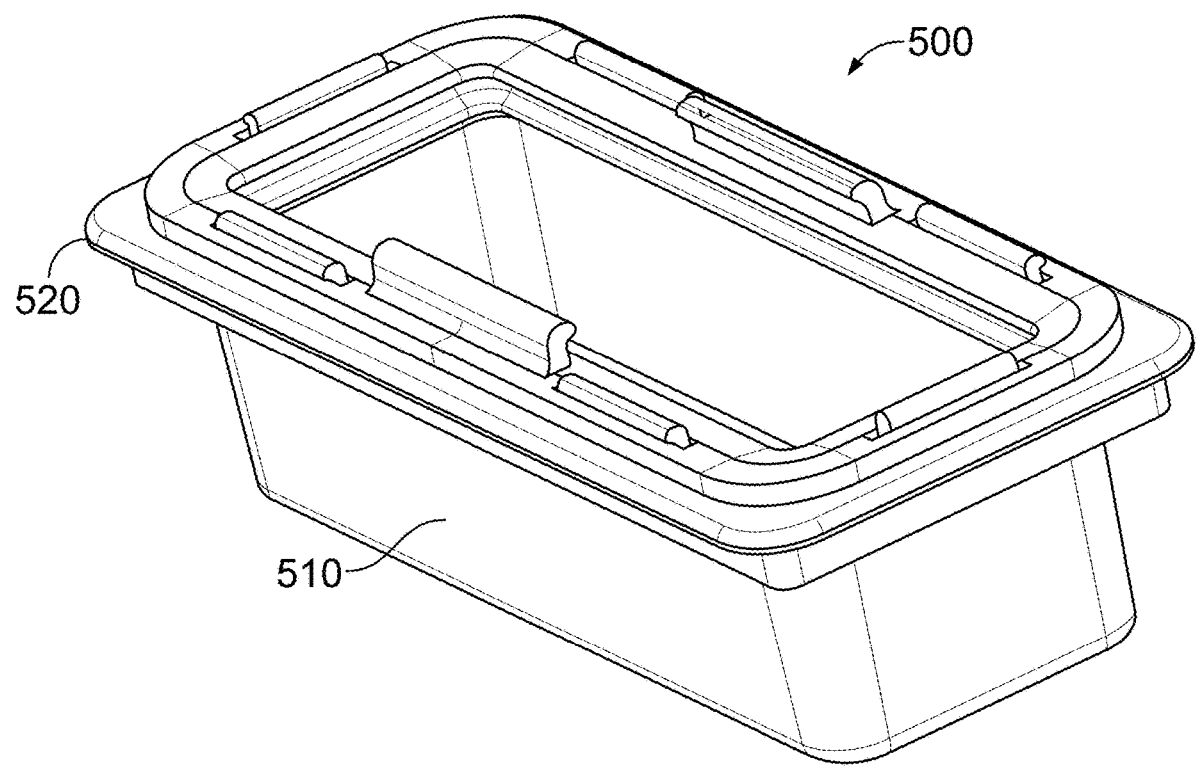
FIG. 5 is a block diagram illustrating an example lid for use in conjunction with sterilizable connector, in accordance with the present disclosure.

FIG. 5 is a block diagram illustrating an example lid for use in conjunction with sterilizable connector, in accordance with the present disclosure. Shown in FIG. 5 is lid 500, which be configured for use in conjunction with sterilizable connectors implemented according to the present disclosure (e.g., connector 200 of FIG. 2).

Figure 6:
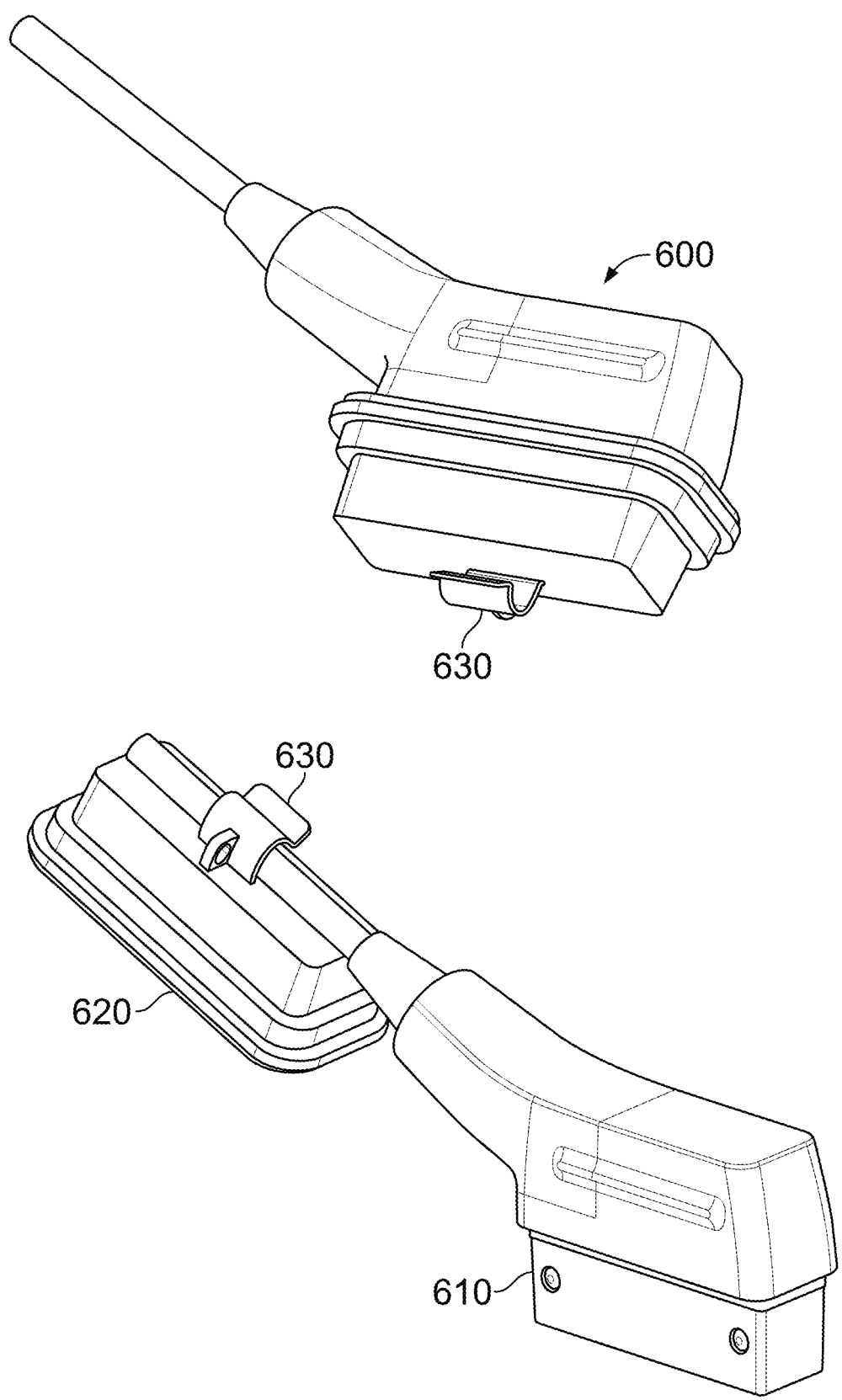
FIG. 6 is a block diagram illustrating an example lid with latching element, for use in conjunction with sterilizable connector, in accordance with the present disclosure.

The lid 500 may comprise only two parts: lid casing 510 and sealing gasket 520. In this regard, as noted above, lids such as the lid 500 may be configured for use as a low-cost solution, such as it may be replaced regularly (consumable) in order to ensure sealing performance all along the lifetime of the product. For example, as shown in the embodiment illustrated in FIG. 5, the two lips gasket 520 may be included in the lid casing 510 to ensure water-tightness. Further, in some instances hard plastic circle may be incorporated in order to ensure and maintain gasket pressure on the connector. The lid casing 510 may be made using suitable high performance polymer (e.g., thermoplastic vulcanizate (TPV), such as Santoprene). Use of such material in the lid casing may be desirable for its smooth touch and the ability to create lips shapes for sealing FIG. 6 is a block diagram illustrating an example lid with latching element, for use in conjunction with sterilizable connector, in accordance with the present disclosure. Shown in FIG. 6 is sterilizable connector 600 along with lid 620. The connector 600 may be substantially similar to the connector 200 as described above.

The connector 600 may be similar to the connector 200. The lid 620 may be configured for application to sealable mating portion 610 of the connector 600. As shown in FIG. 6, the lid 620 incorporates a latching element 630 that is configured to allow tethering the lid 620 to the connector 600 (e.g., to the cable of the connector 600 as illustrated in FIG. 6), which may help ensure that the lid is not lost. As shown in the example embodiment illustrated in FIG. 6, the latching element 630 may be small structure of suitable shape on the back of the lid allows to lock it on the cable (for storage while RS connector is connected to a console).

Figure 7:
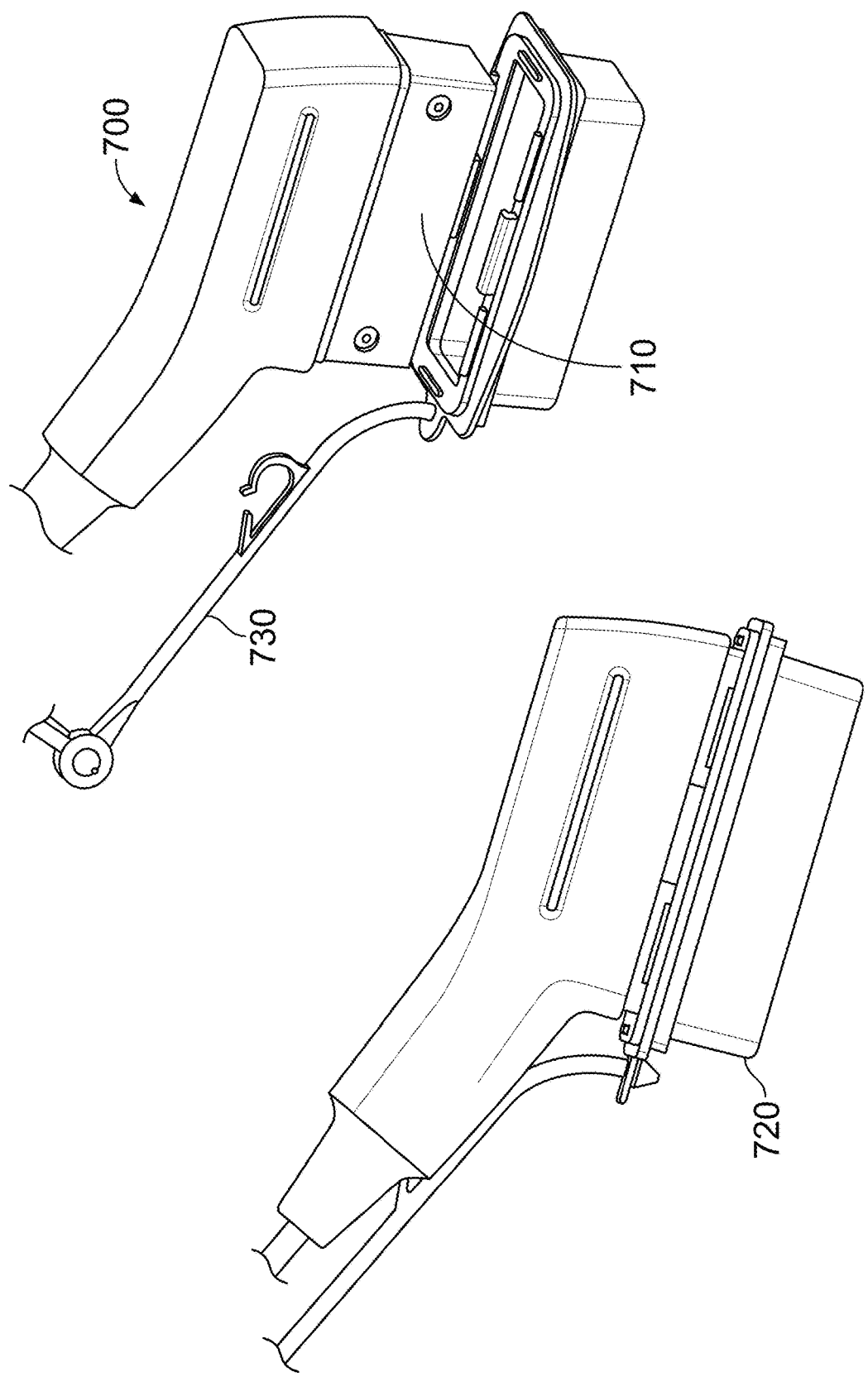
FIG. 7 is a block diagram illustrating an example lid of an alternative design, for use in conjunction with sterilizable connector, in accordance with the present disclosure.

FIG. 7 is a block diagram illustrating an example lid of an alternative design, for use in conjunction with sterilizable connector, in accordance with the present disclosure. Shown in FIG. 7 is sterilizable connector 700 along with lid 720. The connector 700 may be substantially similar to the connector 200 as described above.

The connector 700 may be similar to the connector 200. The lid 720 may be configured for application to a sealable mating portion 710 of the connector 700. As shown in FIG. 7, the lid 720 incorporates a latching element 730 that is configured to allow tethering the lid 720 to the connector 700 (e.g., to the cable of the connector 700 as illustrated in FIG. 7), which may help ensure that the lid is not lost. As shown in the example embodiment illustrated in FIG. 7, the latching element 730 may be a flexible connecting cord (or the like) that is connected to a cable assembly of the connector 700 on one end, and securely engages the lid 720 on the other end, such as using knop-ended stopper structure engaging a loop structure on lid 720, as illustrated in FIG. 7, to prevent the lid 720 from fall off of the latching element. Is some instances, the latching element 730 may comprise a rotating hinge to further enhance flexibility, as illustrated in FIG. 7. Further, in some instances, the latching element 730 may comprise a (e.g., hook, as illustrated in FIG. 7, or the like) to secure the latching element 730 when the lid 720 is applied to a sealable mating portion 710, as illustrated in FIG. 7.

An example connector assembly, in accordance with the present disclosure, configured for use in a medical device to connect a first component of the medical device to a second component of the medical device, comprises a connector that comprises: a first shell and a second shell, wherein the first shell and the second are configured to engage one another; a nose housing that comprises a mating area of the connector for engaging a corresponding mating area in one of the first component and the second component; and an overmolding that overmolds a combination of the first shell, the second shell, and the nose housing; wherein: each of the first shell, the second shell, and the nose housing comprises a first material that is compatible with cleaning and sterilization (C&S) treatment; and the overmolding comprises a second material that provides sealing of the combination of the first shell, the second shell, and the nose housing during the cleaning and sterilization (C&S) treatment.

In an example embodiment, the connector is configured to enable applying at least sterilization without requiring closing or covering of the mating area of the connector.

In an example embodiment, the first material comprises a polymer.

In an example embodiment, the polymer comprises at least one of polypropylene and polycarbonate.

In an example embodiment, the second material comprises a thermoplastic polymer.

In an example embodiment, the thermoplastic polymer comprises thermoplastic vulcanizate (TPV).

In an example embodiment, the connector further comprises one or more shielding shells configured to provide shielding of electrical components and/or circuitry of the connector disposed within the connector.

In an example embodiment, each of the one or more shielding shells comprises stamped metal foil.

In an example embodiment, the connector assembly further comprises a lid configured for engaging and sealing the mating area of the connector.

In an example embodiment, the lid engages and seals the connector without use of locking mechanism or components.

In an example embodiment, the lid is configured to enable applying cleaning processing that is compliant with one or more liquid ingress protection ratings.

In an example embodiment, the one or more liquid ingress protection ratings comprise at least one of Ingress Protection Code IPX6 and Ingress Protection Code IPX7.

In an example embodiment, the lid comprises at least a lid casing and a sealing component that seals contact between the lid and at least a portion of the connector.

In an example embodiment, the lid casing comprises same material as the second material used in the overmolding.

In an example embodiment, the medical device comprises a medical imaging device.

In an example embodiment, one of the first component and the second component comprises a medical imaging probe.

As utilized herein the terms "circuits" and "circuitry" refer to physical electronic components (e.g., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z." As utilized herein, the terms "block" and "module" refer to functions than can be performed by one or more circuits. As utilized herein, the term "exemplary" means serving as a non-limiting example, instance, or illustration. As utilized herein, the terms "for example" and "e.g.," set off lists of one or more non-limiting examples, instances, or illustrations. As utilized herein, circuitry is "operable" to perform a function whenever the circuitry comprises the necessary hardware (and code, if any is necessary) to perform the function, regardless of whether performance of the function is disabled or not enabled (e.g., by some user-configurable setting, a factory trim, etc.).

Other embodiments of the invention may provide a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the processes as described herein.

Accordingly, the present disclosure may be realized in hardware, software, or a combination of hardware and software. The present invention may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip.

Various embodiments in accordance with the present disclosure may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A connector assembly configured for use in a medical device to connect a first component of the medical device to a second component of the medical device, the connector assembly comprising:
   a connector that comprises:
      a first shell and a second shell, wherein the first shell and the second are configured to engage one another;
      a nose housing that comprises a mating area of the connector for engaging a corresponding mating area in one of the first component and the second component; and
      an overmolding that overmolds a combination of the first shell, the second shell, and the nose housing;
   wherein:
      each of the first shell, the second shell, and the nose housing comprises a first material that is compatible with cleaning and sterilization (C&S) treatment of medical equipment; and
      the overmolding comprises a second material that provides sealing of the combination of the first shell, the second shell, and the nose housing during the cleaning and sterilization (C&S) treatment; and
   a lid configured for engaging the connector, wherein the lid is configured to seal the mating area of the connector during the cleaning and sterilization (C&S) treatment.

2. The connector assembly of claim 1, wherein the connector is configured to enable applying at least sterilization without requiring closing or covering of the mating area of the connector.

3. The connector assembly of claim 1, wherein the first material comprises a polymer.

4. The connector assembly of claim 3, wherein the polymer comprises at least one of polypropylene and polycarbonate.

5. The connector assembly of claim 1, wherein the second material comprises a thermoplastic polymer.

6. The connector assembly of claim 5, wherein the thermoplastic polymer comprises thermoplastic vulcanizate (TPV).

7. The connector assembly of claim 1, wherein the connector further comprises one or more shielding shells configured to provide shielding of electrical components and/or circuitry of the connector disposed within the connector.

8. The connector assembly of claim 7, wherein each of the one or more shielding shells comprises stamped metal foil.

9. The connector assembly of claim 1, wherein the lid engages and seals the connector without use of locking mechanism or components.

10. The connector assembly of claim 1, wherein the lid is configured to enable applying cleaning processing that is compliant with one or more liquid ingress protection ratings.

11. The connector assembly of claim 10, wherein the one or more liquid ingress protection ratings comprise at least one of Ingress Protection Code IPX6 and Ingress Protection Code IPX7.

12. The connector assembly of claim 1, wherein the lid comprises at least a lid casing and a sealing component that seals contact between the lid and at least a portion of the connector.

13. The connector assembly of claim 12, wherein the lid casing comprises same material as the second material used in the overmolding.

14. The connector assembly of claim 1, wherein the medical device comprises a medical imaging device.

15. The connector assembly of claim 14, wherein one of the first component and the second component comprises a medical imaging probe.

16. The connector assembly of claim 1, wherein one or both of the first material and the second material are selected based on selection criteria that comprise being resistant to material or chamicals used in the cleaning and sterilization (C&S) treatment.

* * * * *